United States Patent [19]

Edwards

[11] Patent Number: 4,464,800
[45] Date of Patent: Aug. 14, 1984

[54] ATTACHMENT DEVICE FOR MOUNTING FACE-PROTECTIVE SHIELDS ON HEADGEAR

[76] Inventor: David B. Edwards, 762 S. Redwood Rd., Salt Lake City, Utah 84125

[21] Appl. No.: 406,041

[22] Filed: Aug. 20, 1982

[51] Int. Cl.³ .............................................. A61F 9/02
[52] U.S. Cl. .............................................. 2/452; 2/8; 2/451
[58] Field of Search ...................... 2/8, 417, 421, 422, 2/452, 451, 453; 411/531, 546

[56] References Cited

U.S. PATENT DOCUMENTS 2,283,120  5/1942  Malcom ................................... 2/8

Primary Examiner—Werner H. Schroeder
Assistant Examiner—J. L. Kravitz
Attorney, Agent, or Firm—Philip A. Mallinckrodt; Robert R. Mallinckrodt

[57] ABSTRACT

In an attachment device for use in pairs to mount a face-protective shield, such as a welding helmet, for lifting and lowering pivotal movement on a headgear, the provision of two separate pieces adapted for interfitted engagement relative to each other at longitudinally adjusted positions determined by the requirements of the particular make of headgear and face shield concerned. One of the pieces has a tubular boss projecting therefrom, while the other piece has an elongate slot through which the boss extends. Interengaging means, such as respective series of saw-like teeth, are provided on confronting faces of the two pieces, whereby the positions of the two pieces relative to each other can be adjusted to place the boss as may be required by the position of a boss-receiving opening in a side wall of a particular make of face-protective shield.

12 Claims, 7 Drawing Figures

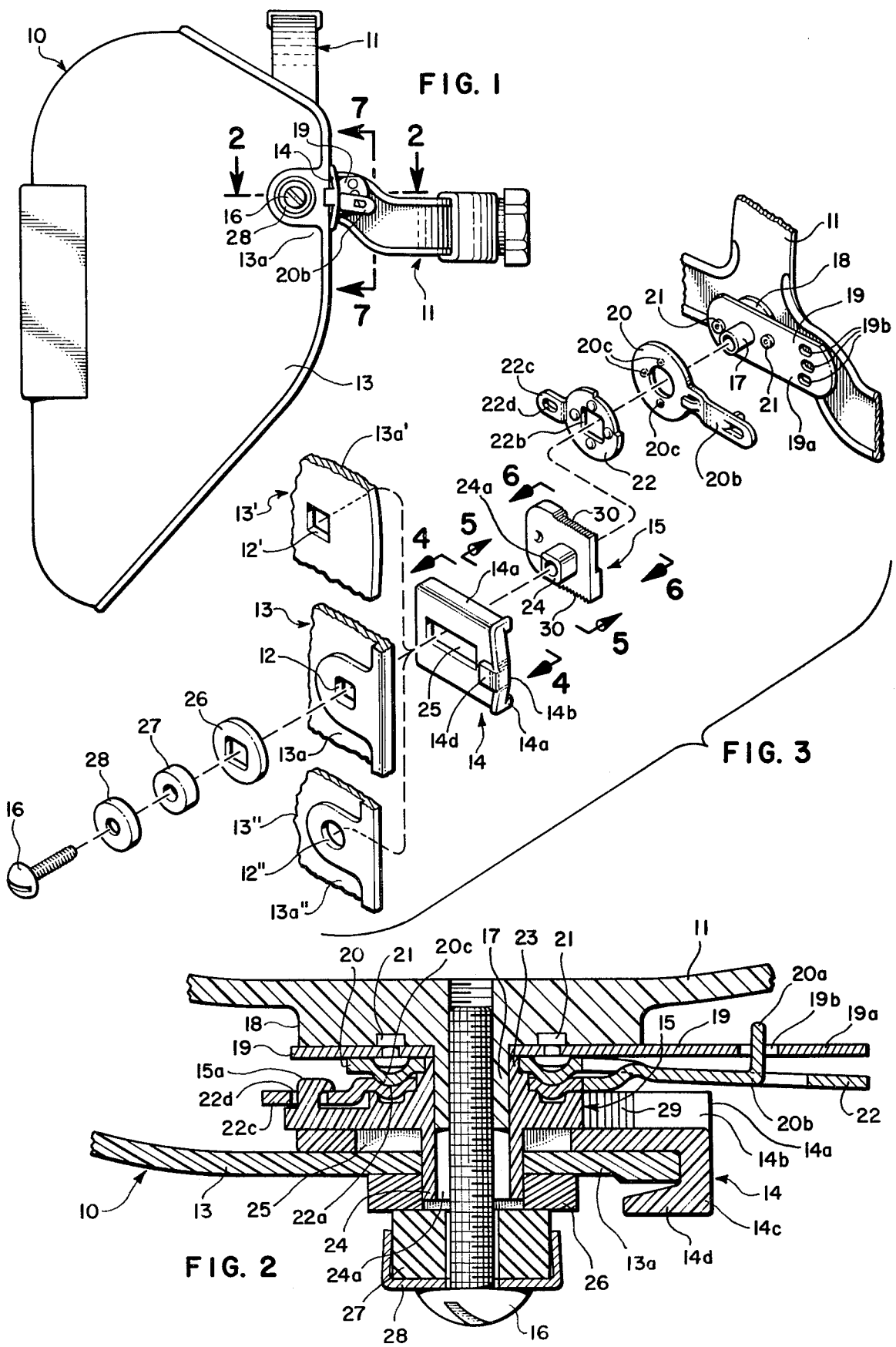

ATTACHMENT DEVICE FOR MOUNTING FACE-PROTECTIVE SHIELDS ON HEADGEAR

FIELD

This invention is in the field of devices for attaching face-protective shields, such as welding helmets, to special headgear constructed for having such shields mounted thereon.

BACKGROUND OF THE INVENTION

In the art of welding, it is customary for a welder to wear headgear on which is pivotally mounted a face-protective shield, usually in the form of a so-called "welding helmet" that has a window through which the welder watches the course of the work. The headgear is usually an open band structure adapted to fit comfortably on the head of the welder and to hold the welding helmet in front of his face during a welding operation, with the window at proper eye level. Various types of attachment devices have been developed in the past for mounting welding helmets on band types of headgear or on hard hats, which are occasionally worn during welding instead of the band type of headgear. Among these prior attachment devices are those shown in G. Z. Edwards et al. U.S. Pat. Nos. 2,963,709; 2,973,522; and 3,074,072; and those shown in the U.S. patents to C. E. Bowers, U.S. Pat. No. 2,658,200; G. R. Hoffmaster, U.S. Pat. No. 2,747,191; W. E. Newcomb, U.S. Pat. No. 3,430,263; and Heinz E. Ruck, U.S. Pat. No. 3,866,244. None of these, however, provide for the mounting of welding helmets of different manufacturers onto the same make of headgear, it being realized that the mounting openings in the helmets of different manufacturers are placed at different distances from the edges of the helmets and are not always the same shape.

OBJECTIVE OF THE INVENTION

It is the principal objective of the present invention to provide an attachment device that can be made to properly mount the face-protective shield, especially a welding helmet, of different manufacturers onto the same make of headgear.

SUMMARY OF THE INVENTION

In accordance with the invention, attachment devices of the type concerned have two members adapted for interfitted engagement relative to each other at longitudinally adjusted positions which are determined by the requirements of the particular makes of headgear and face shield involved. Interengagement means, preferably in the form of mutually opposite and confronting series of interengaging teeth, are provided on confronting faces of the members, respectively, preferably on confronting edge faces, and one of the members is provided with a tubular boss for extending through the usual attachment opening in the face shield and for receiving an attachment screw in its extension into threaded engagement with an internally threaded boss projecting outwardly from the headgear, while the other member is elongate and provided with an elongate, boss-accommodating slot.

Such slot enables the boss of the one member to extend through the other member and, thus, through the attachment opening in the corresponding side wall of the face shield, regardless of the particular adjusted interpositioning of the two members necessitated by the position of such opening in the face shield. By making such boss square and of a size adapted to fit the standard square attachment opening of a face shield such as a welding helmet, it can also be used with the standard round attachment openings of other makes of face shields.

When the face shield is a welding helmet, the slotted, elongate member of the attachment device preferably has an outwardly projecting lip at one end for receiving a corresponding edge margin of the welding helmet and for thereby serving as a limit stop and placement means for such member relative to the helmet. The other member preferably has an oppositely-projecting pin adjacent to its opposite end for engagement with pivotal detent mechanism commonly forming part of headgear attachment devices.

THE DRAWINGS

In the drawings, which illustrate an attachment device constituting the best mode presently contemplated for carrying out the invention with respect to one make of headgear:

FIG. 1 is a left side elevational view of a typical welding helmet of one manufacturer mounted by means of the attachment device of the invention on a typical band-type of headgear put out by a different manufacturer, with the helmet positioned in face-protective position relative to the headgear;

FIG. 2, a fragmentary horizontal section taken on the line 2—2 of FIG. 1 and drawn to a considerably larger scale;

FIG. 3, an exploded view in perspective showing the individual parts of the left-hand attachment device of the invention shown in FIG. 1 and how they are arranged with respect to the corresponding pivoting mechanism of the particular headgear shown and to differing attachment holes in the helmets of three different manufacturers;

FIG. 4, a full face view looking toward the inside face of the outer piece of the illustrated attachment device, as taken from the standpoint of the line 4—4 of FIG. 3;

FIG. 5, a full face view of the confronting face of the inner piece of such attachment device, as viewed from the standpoint of the line 5—5 in FIG. 3;

FIG. 6, a similar full face view of the reverse face of such inner piece, taken from the standpoint of the line 6—6 in FIG. 3; and FIG. 7, a fragmentary vertical section taken on the line 7—7 of FIG. 1 and drawn to the scale of FIG. 2, showing the attachment device of the invention in end elevation.

DETAILED DESCRIPTION OF THE ILLUSTRATED EMBODIMENT

Figure 4:
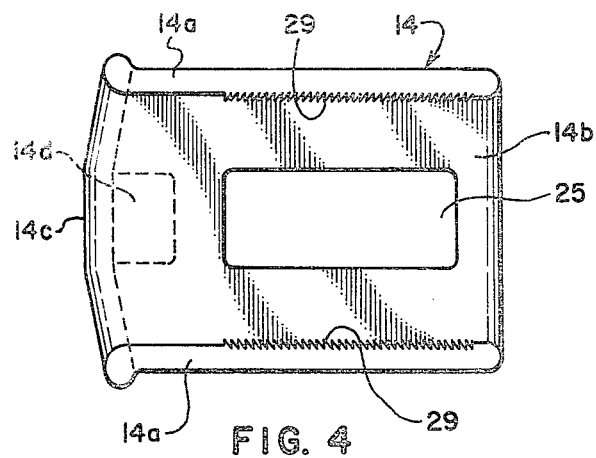

In the illustrated embodiment, a welding helmet 10 is attached to a band type of headgear 11, as a face-protective shield, by the attachment device of the invention. Normally both helmet and headgear are produced by the same manufacturer along with attachment components, and there is no problem in attaching the helmet to the headgear. In many instances, however, as previously indicated, a welder having the headgear of one manufacturer may wish to use the helmet of a different manufacturer. The attachment device of the invention enables this to be done, the structural details being in accord with the design of the particular headgear concerned.

It is primarily the locations and shapes of the attachment openings, see 12, 12', and 12'', FIG. 3, in the margins, see 13a, 13a', and 13a'', FIG. 3, of respectively opposite side walls of the helmet, nearer to or farther from the edges of such side walls, that differ in helmets (see 13, 13', and 13'', FIG. 3) of different manufacturers and prevents effective attachment to non-conforming headgear.

In order to accommodate such differences in location, as well as shapes of the attachment openings, the attachment device of the invention (one being required for each side wall of the helmet) comprises two separate, adjustably interfitting, elongate pieces 14 and 15, respectively, provided with rows of interengagement means, respectively, extending longitudinally thereof. One of these pieces, here the piece 14, is adapted for engagement with the helmet, while the other, here the piece 15, is adapted for engagement with the headgear. One, here the piece 14, is provided with an elongate slot for accommodating a projecting, tubular boss from the other, through which extends the usual attachment screw 16 that threadedly engages the usual internally threaded, tubular boss 17 projecting outwardly from the headgear.

In the illustrated embodiment, boss 17 and a platform 18, from which it projects, are molded integrally of the same plastic material from which the headgear 11 is molded and integrally with such headgear. The usual base plate 19, with rearwardly extending arm 19a having anchor holes 19b for selective positioning of the anchoring projection 20a of the rearwardly extending arm 20b of the usual headgear detent lock plate 20, is rigidly fastened to platform 18 by rivets 21. Boss 17 extends through a receiving opening in base plate 19.

Figure 5:
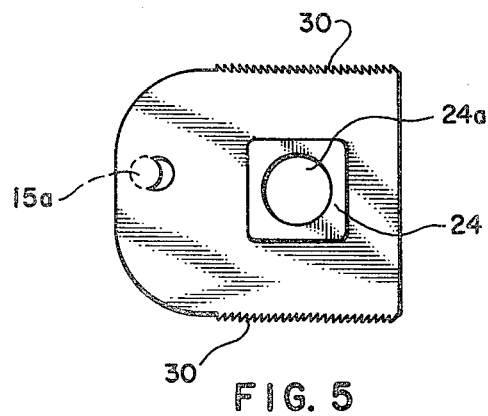
Figure 7:
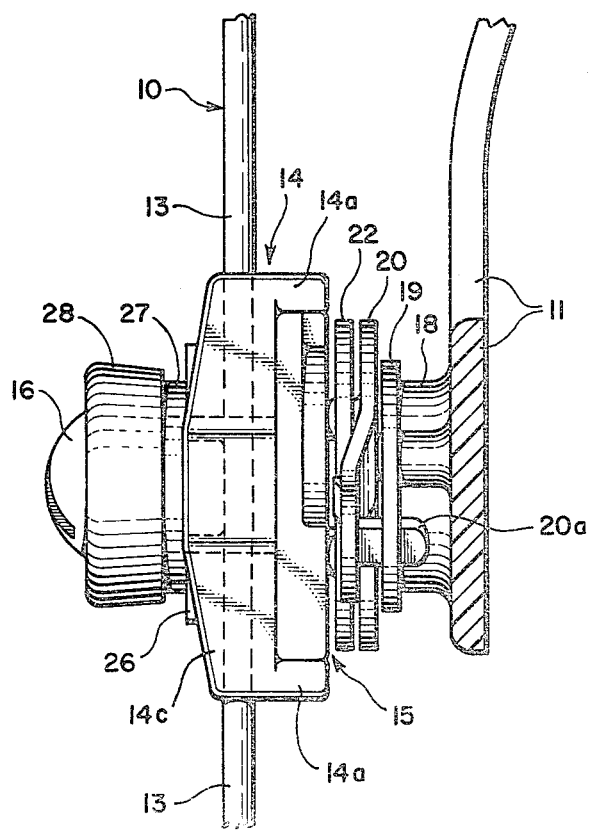
Figure 6:
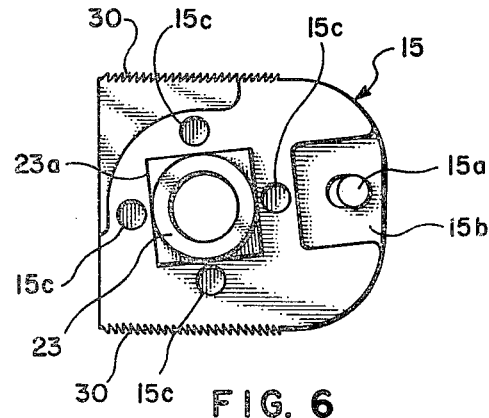

A helmet detent lock plate 22, usual for this make of headgear, whose detent recesses 22a, FIG. 2, are engaged by detent dimples 20c, FIG. 3, of the usual headgear detent lock plate 20, has a central square opening 22b, therethrough, which fits over the square, receiving base 23a, FIG. 6, of a circular, tubular boss 23, see also FIG. 2, projecting from the headgear-facing side of the piece 15, being thus attached to such piece 15 for pivotal movement therein about the axis of headgear boss 17 to which the attachment device is secured by screw 16 passing through tubular boss 23. Lock plate 22 is preferably of resilient metal, having an arm 22c, FIGS. 2 and 3, offset from the plane thereof and extending therefrom rearwardly of the headgear and helmet when installed, with a slot 22d that engages a retention post 15a, FIGS. 2 and 5, of piece 15 in a snap fit that normally retains lock plate 22 conveniently in place on piece 15 even when the attachment device is disassembled.

Piece 15 is advantageously molded from a suitable plastic material, such as nylon, with post 15a, FIGS. 5 and 6, projecting from the bottom of a recess 15b, FIG. 6, that is shaped to receive arm 22c of lock plate 22 when it is snapped onto post 15a. As so positioned on piece 15, with square opening 22b fitted over square base 23a of boss 23 of such piece 15, as shown in FIG. 2, the dimple backs of detent recesses 22a are accommodated by recesses 15c of piece 15.

Projecting from the face of piece 15 opposite that from which tubular boss 23 projects, concentrically with such tubular boss and integrally with piece 15, is a square boss 24, FIGS. 2, 3 and 5, having a circular bore 24a extending therethrough for accommodating passage of attachment screw 16.

Piece 14, into which piece 15 fits in positional adjustment relative thereto selected to fit the particular welding helmet, see 13, 13', and 13'', FIG. 3, concerned, is slotted longitudinally, as at 25, to receive boss 24 in any of the possible adjusted positions of piece 25 relative to piece 14, as can be seen in FIG. 2. After passing boss 24 of the assembled attachment device through the receiving opening 12, 12', or 12'' of the helmet, here the receiving opening 12 of the helmet 10, a rigid washer 26 is applied over the projecting end of such boss 24, and screw 16 is passed therethrough after installation thereon of an elastomer washer 27 and a rigid cap 28. Screw 16 engages the internal threads of headgear boss 17 and platform 18 and is cinched to a tightness which maintains helmet 10 in place, raised or lowered, but permits pivotal movement of it and the attachment device of the invention relative to headgear 11 and about headgear boss 17 for raising the helmet from a lowered work position to an out-of-the-way position, above the head, and back to the lowered work position that protects the face and the eyes from glare.

In accordance with the invention, the pieces 14 and 15 of the attachment device are provided, longitudinally thereof, with interengagement means for positional adjustment of piece 15 relative to piece 14. In the illustrated embodiment, these take the form of mutually opposite and confronting series 29, FIG. 4, and 30, FIGS. 5 and 6, of interengaging teeth advantageously of saw-like configuration on confronting edge faces of the two pieces. For this purpose, outer piece 14 is formed as a substantially flat plate with mutually opposite side members 14a extending longitudinally of such piece at and along the inside face thereof to provide a shallow recess 14b, FIGS. 2, 3, 4, and 7, for receiving piece 15. The series of teeth 29 are formed along the inner faces of the side members 14a, and the series of teeth 30 are formed along the edge faces of piece 15 that confront such inner faces when the two pieces are brought together in face-to-face relationship.

Piece 14 is preferably provided with an end wall 14c, FIGS. 2 and 4, from which a tab member 14d extends to provide a hook formation for receiving the forward edge margin of the helmet, here 13, as in FIG. 2.

Whereas this invention is here illustrated and described with specific reference to an embodiment thereof presently contemplated as the best mode of carrying out such invention in actual practice, it is to be understood that various changes may be made in adapting the invention to different embodiments without departing from the broader inventive concepts disclosed herein and comprehended by the claims that follow.

I claim:

1. An attachment device for mounting a face-protective shield, such as a welding helmet, on receiving headgear provided with internally threaded openings at opposite sides thereof for threaded engagement by attachment screws, said shield being provided with attachment-screw-accommodating openings adapted for axial alignment with said internally-threaded openings, respectively, in the screw attachment of face shield to headgear, said attachment device comprising two separate, mutually elongate and non-rotatable pieces adapted for interfitted engagement with each other at selected, longitudinally adjusted positions which are determined by the requirements of the particular headgear and face shield concerned to enable one to accommodate the other, and being provided, further, with confronting faces, respectively, one of said pieces having a tubular boss at one face thereof for extending through a corresponding attachment opening of the face-protective shield and for receiving an attachment screw, and the other of said pieces having an elongate, boss-accommodating slot extending longitudinally thereof; and longitudinally-extending, interengagement means carried by said confronting faces of said pieces for interengagement at adjusted positions of said pieces relative to each other.

2. An attachment device in accordance with claim 1, wherein the said confronting faces of the pieces of the attachment device are lateral edge faces of the respective pieces.

3. An attachment device in accordance with claim 1, wherein the said one of the pieces is formed to receive, in axial alignment with the tubular boss, an outwardly projecting tubular boss of the headgear, through which extends one of the internally threaded, attachment-screw-engaging openings of the headgear.

4. An attachment device in accordance with claim 1, additionally including an attachment screw, a rigid washer for said screw adapted for placement against the outside wall surface of the face-protective shield, and an elastomer washer having a rigid covering cap for said attachment screw so said elastomer washer will bear against said rigid washer when said attachment screw is in place.

5. An attachment device in accordance with claim 1, wherein the said other of the pieces is formed as a substantially flat plate with mutually opposite side members extending longitudinally of and projecting from confronting face thereof; and wherein the said one of the pieces is formed as a substantially flat plate for fitting face-to-face against said other piece between said side members thereof.

6. In combination, a headgear; a face-protective shield pivotally mounted on said headgear for raising above the head of a wearer and for lowering over the face; and a pair of attachment devices, each in accordance with claim 1, pivotally attaching said shield to said headgear at opposite sides thereof, respectively.

7. An attachment device in accordance with either claim 1 or 2, wherein the interengagement means are in the form of mutually opposite and confronting series of interengaging teeth.

8. An attachment device in accordance with either claim 1 or 2, wherein the interengagement means are in the form of mutually opposite and confronting series of saw-like teeth arranged for interengagement.

9. An attachment device in accordance with claim 3, wherein the said one of the pieces has an extension of the tubular boss at its opposite face for receiving the outwardly projecting tubular boss of the headgear.

10. An attachment device in accordance with claim 1 or 3, wherein the said one of the pieces is provided with means for interengagement with mating means of a face shield detent lock plate associated with the headgear, so said lock plate will be held in place on said one of the pieces when the attachment device is disassembled after having been installed.

11. An attachment device in accordance with claim 5, wherein a hook member is formed at one end of the said one of the pieces and projects from the face thereof which is opposite the said confronting face thereof for receiving an edge margin of the face shield when installed.

12. An attachment device in accordance with claim 9, wherein the said specified extension of the tubular boss is outwardly configurated, at its base, to receive and hold, against rotation, a detent lock plate associated with the headgear and is otherwise cylindrically configurated to rotatably receive a second detent lock plate associated with the headgear and arranged to interlock with the first detent lock plate.

* * * * *